(12) United States Patent
Schramm et al.

(10) Patent No.: US 9,980,747 B2
(45) Date of Patent: May 29, 2018

(54) RETRACTABLE CENTESIS NEEDLE

(71) Applicant: Argon Medical Devices, Inc., Plano, TX (US)

(72) Inventors: John B. Schramm, Skokie, IL (US); Kevin Hess, Chicago, IL (US); Sophie Marcoux, Gainesville, FL (US)

(73) Assignee: Argon Medical Devices, Inc., Plano, TX (US)

( * ) Notice: Subject to any disclaimer, the term of this patent is extended or adjusted under 35 U.S.C. 154(b) by 298 days.

(21) Appl. No.: 14/941,443

(22) Filed: Nov. 13, 2015

(65) Prior Publication Data
US 2017/0135726 A1     May 18, 2017

(51) Int. Cl.
| | | |
|---|---|---|
| *A61B 17/34* | (2006.01) |
| *A61M 39/24* | (2006.01) |
| *A61M 25/06* | (2006.01) |
| *A61M 27/00* | (2006.01) |
| *A61M 1/00* | (2006.01) |

(52) U.S. Cl.
CPC ...... *A61B 17/3496* (2013.01); *A61B 17/3415* (2013.01); *A61B 17/3421* (2013.01); *A61B 17/3498* (2013.01); *A61M 1/0068* (2014.02); *A61M 25/065* (2013.01); *A61M 27/00* (2013.01); *A61M 39/24* (2013.01); *A61B 2017/3456* (2013.01); *A61M 2205/584* (2013.01)

(58) Field of Classification Search
CPC .......... A61M 1/0068; A61M 2205/584; A61M 25/065; A61M 27/00; A61M 39/24; A61M 25/0643; H01H 2235/03; A61B 17/3415; A61B 17/3421; A61B 17/3496; A61B 17/3498; A61B 2017/3456
See application file for complete search history.

(56) References Cited

U.S. PATENT DOCUMENTS

| | | | |
|---|---|---|---|
| 4,447,235 A | | 5/1984 | Clarke |
| 4,525,611 A | * | 6/1985 | Akamatsu ......... H01H 35/2614 200/83 J |
| 4,831,223 A | * | 5/1989 | Wako ................ H01H 13/20 200/290 |
| 4,958,625 A | * | 9/1990 | Bates .................. A61B 10/0275 600/562 |
| 5,114,186 A | * | 5/1992 | Sugiyama ............ A63C 11/221 280/821 |
| 5,224,470 A | * | 7/1993 | Schnepp-Pesch .. A61B 10/0283 600/566 |
| 5,256,148 A | | 10/1993 | Smith et al. |

(Continued)

*Primary Examiner* — Adam Marcetich
(74) *Attorney, Agent, or Firm* — IpHorgan Ltd.

(57) ABSTRACT

A retractable centesis needle comprises a hollow, sharp tipped outer cannula extending from a housing. The outer cannula is generally tube-like and open at both ends to form a channel into a cavity in the housing. A blunt tipped inner cannula is disposed within the channel and capable of sliding away from the housing to an extended state and toward the housing to a refracted state. The inner cannula is biased toward the extended state by a first spring disposed in the housing. A second spring also disposed in the housing acts in the same direction as the first spring when the inner cannula is in a fully retracted state. However, the second spring does not bias the inner cannula in any direction when the inner cannula is in a fully extended state.

20 Claims, 5 Drawing Sheets

(56) References Cited

U.S. PATENT DOCUMENTS

| | | | |
|---|---|---|---|
| 5,334,159 A | | 8/1994 | Turkel |
| 5,669,883 A | | 9/1997 | Scarfone et al. |
| 5,685,852 A | * | 11/1997 | Turkel ............... A61B 17/3401 604/159 |
| 6,176,208 B1 | * | 1/2001 | Tsuzuki ................. F01L 1/462 123/90.11 |
| 6,447,483 B1 | | 9/2002 | Steube et al. |
| 6,638,251 B2 | | 10/2003 | Steube et al. |
| 6,668,406 B2 | * | 12/2003 | Spinks ............... A47C 23/0433 5/256 |
| 8,840,588 B2 | | 9/2014 | Clement et al. |
| 2006/0052809 A1 | * | 3/2006 | Karbowniczek ..... A61B 5/1411 606/181 |
| 2012/0209203 A1 | * | 8/2012 | Gibertoni ........... A61B 17/3415 604/164.11 |
| 2013/0310750 A1 | * | 11/2013 | Hopman ............... A61M 1/008 604/159 |
| 2014/0046303 A1 | * | 2/2014 | Donaldson ......... A61B 17/3415 604/540 |

* cited by examiner

RETRACTABLE CENTESIS NEEDLE

FIELD OF THE INVENTION

The present invention relates to a retractable needle device for centesis, and more particularly a device for insertion of a drainage catheter for draining fluid from a body cavity of a patient.

BACKGROUND OF THE INVENTION

It is a routine medical procedure to insert a drainage catheter into a patient to remove excess fluid from a body cavity. For example, when excess fluid builds up in the pleural cavity, the fluid can prevent a lung from expanding normally, impairing breathing. Thoracentesis is a procedure to remove the fluid by placing a drainage catheter within the pleural space. During the procedure, several layers of body tissue must be penetrated to position the tip of the catheter, and the user must take care to avoid puncturing the lung itself.

Retractable centesis needle devices typically include a cannula with a sharp tip to cut through tissue walls and allow the device to be positioned within a body cavity. Some retractable centesis needles such as U.S. Pat. No. 4,447,235 include a retractable blunt needle positioned inside the cannula. In those devices, the blunt needle extends beyond the cutting edge of the cannula to prevent the user from inadvertently cutting or piercing through tissues during maneuvering. The action of the needle retracting may also provide visual, auditory, or haptic feedback when the blunt needle makes contact with tissue. The needle may be automatically retracted as the device is pressed against tissue by coupling the needle to a spring or other biasing member.

Retractable centesis needles may also include visual indicators. For example, the retractable needle device of U.S. Pat. No. 5,256,148 includes two regions colored in different colors. A section of the needle is viewable through a lens in the housing. As the needle is retracted, the colored portion of the needle visible in the lens changes. The change in color enables the user to estimate how far the needle has retracted into the sharp cannula while the device is obscured inside the patient's body.

Other devices seek to improve upon the design of U.S. Pat. No. 5,256,148 by improving the sensitivity of the indicating system. U.S. Pat. No. 6,447,483 describes a device that includes two opposing springs coupled to the retractable needle to bias it in opposite directions. The opposing-spring configuration is intended to decrease the initial resisting force at which the indicator is displaced as compared to a single spring of a similar size, alerting a physician more quickly when a tissue wall is contacted.

Although the initial force required to begin displacing the indicator is lower in the opposing spring system, the required force increases at a faster rate than the single spring alone. In other words, although the resisting force required to begin revealing the indicator is lower, a greater change in resisting force is required to reveal the entire indicator. A need therefore exists for a device that provides increased initial sensitivity until the indicator is revealed, and decreased sensitivity after the indicator is revealed. In addition, the springs in an opposing spring system work against one another, with the springs being in a compressed state even during a static state prior to use. The excess forces exerted inside the opposing spring device may weaken or deform the device components. Therefore, a need exists for a device that reduces spring forces during a static state prior to use.

The three US patents described above are herein incorporated by reference in their entirety.

SUMMARY OF THE INVENTION

The present invention overcomes the problems in the prior art by providing a device with high initial sensitivity until contact is achieved and with high resistance after contact is achieved.

In summary, the present invention comprises a hollow, sharp tipped outer cannula extending from a housing. The outer cannula is generally tube-like and open at both ends to form a channel into a cavity in the housing. A blunt tipped inner cannula is disposed within the channel and capable of sliding away from the housing to an extended state and toward the housing to a retracted state. The inner cannula is biased toward the extended state by a first biasing member disposed in the housing. A second biasing member also disposed in the housing acts in the same direction as the first biasing member when the inner cannula is in a fully retracted state. However, the second biasing member does not bias the inner cannula in any direction when the inner cannula is in a fully extended state.

The spring arrangement provides a nonlinear force profile designed to increase initial sensitivity to tissue contact, but provide increased resistance once contact occurs. While in the fully extended position, the second spring does not come into association with the inner cannula. The second spring is in a relaxed state and does not contribute to a biasing force on the inner cannula. As the inner cannula continues to retract, however, the second spring comes into association with the inner cannula and begins to compress, providing a biasing force in the same direction as the first spring. Thus, during initial stages of retraction only the first spring contributes to the biasing force, requiring a lower force to move the inner cannula and thereby increasing sensitivity. However, during later stages of retraction, both the first and second spring contribute to a biasing force, requiring a higher force to move the inner cannula and thereby increasing resistance to exposure of the sharp tip. In practice, the device according to the present invention will quickly signal to the user that the blunt tip of the device has contacted resisting tissue and will also require a higher force to expose the sharp tip to puncture the tissue, thereby reducing the risk of unintentional puncture.

It is therefore an object of the present invention to provide a retractable centesis needle having a visual indicator with improved sensitivity to a resisting force.

A further object of the present invention is to indicate when the tips of the outer and inner cannulas are aligned.

It is still a further object of the present invention to provide an outer cannula with a soft outer edge in order to reduce the likelihood of damage to a plastic catheter during loading.

DETAILED DESCRIPTION OF THE INVENTION

Figure 1:
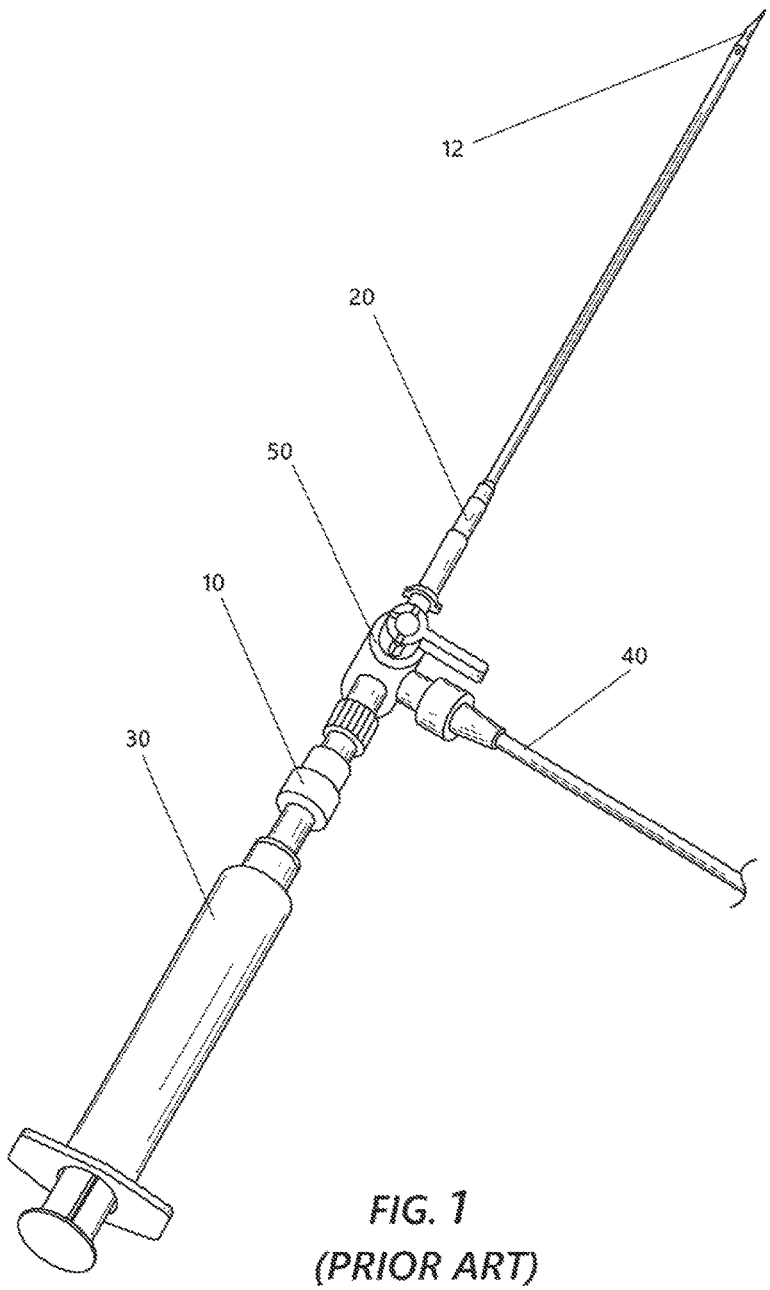
FIG. 1 is a perspective view of a prior art centesis system.

A retractable centesis needle may be used as part of a larger system for a centesis procedure. FIG. 1 illustrates a prior art centesis system. Generally, a retractable centesis needle 10 is used to aid insertion of a flexible catheter 20 into a patient's body. The retractable centesis needle 10 includes a sharp and rigid insertion needle 12 for penetrating body tissue and guiding the flexible catheter 20 to the correct location. A syringe 30 may be connected to the proximal end of the retractable centesis needle 10 typically through a luer-type connection. In order to verify correct placement of the catheter 20, an operator may use the syringe 30 to generate suction and draw a small amount of fluid through the insertion needle 12. Once placement is verified, the retractable centesis needle 10 and syringe 30 can be removed, and a drainage line 40 can be connected to the catheter 20. A stopcock 50 or similar valve may be used between the catheter 20 and retractable centesis needle 10 to control flow when the retractable centesis needle is removed. The drainage line 40 can be connected to an additional outlet on the stopcock 50 and the stopcock operated to channel the fluid between the catheter 20 and drainage line 40. A check valve (not shown) may be placed between the stopcock 50 and the retractable centesis needle 10. The check valve (not shown) may include a means for preventing reinsertion of the retractable centesis needle 10 after it has been withdrawn.

Figure 2:
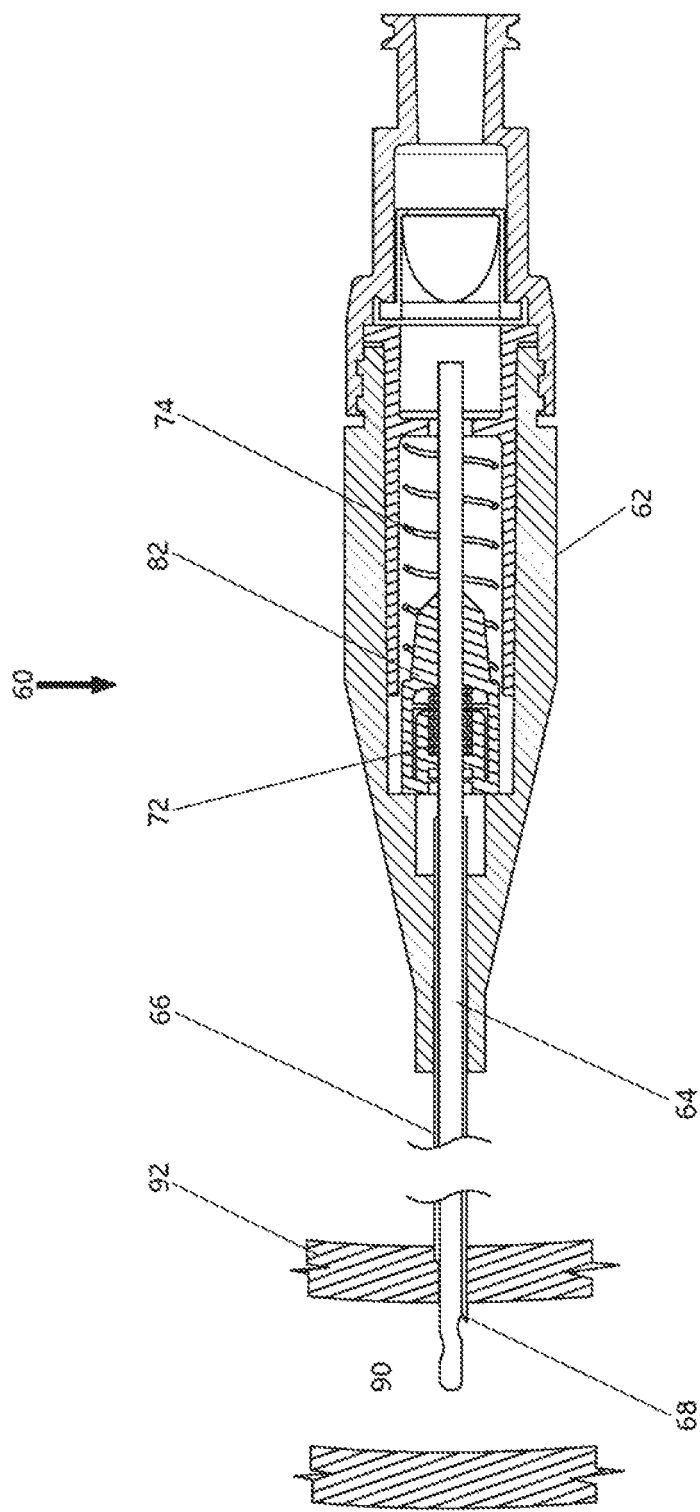
FIG. 2 is a side section view of a prior art retractable centesis needle.

FIG. 2 demonstrates the use of a prior art retractable centesis needle 60 as it is inserted to place a catheter (not shown) into a body cavity 90. The prior art device 60 comprises a housing 62 and a spring-biased inner needle 64 inserted within a hollow outer needle 66. A large spring 74 is connected between the near end of the housing 62 and an indicator 82 connected to the inner needle 64. The large spring 74, being under slight compression, continuously applies a biasing force to the inner needle 64 causing it to protrude from the outer needle 66. A second, smaller spring 72 is connected between the far end of the housing 62 and the indicator 82. The small spring 72 is also under compression, providing a biasing force to the inner needle 64 in opposition to the biasing force of the large spring 74. As the blunt tip of the inner needle 64 is pushed toward an outer tissue wall 92, the tissue resists the blunt tip of the inner needle 64, causing it to retract into the outer needle 66, compressing the large spring 74 and relaxing the small spring 72. As the inner needle 64 continues to retract, the sharp tip 68 of the outer needle 66 becomes exposed, and continued pressure on the device causes the sharp tip 68 to cut through the tissue wall 92. Once the tip 68 of the device has penetrated the tissue and entered the body cavity 90, there is no longer any resistance against the inner needle 64. The large spring 74 begins to relax, compressing the small spring 72 and forcing the inner needle 64 to once again extend beyond the sharp cutting tip 68. FIG. 2 depicts the final stage where the inner needle 64 has extended after penetration of the tissue wall 92. Once the user determines that the device is in the correct position within the cavity 90, the retractable centesis needle may be withdrawn from a catheter. FIG. 2 does not show the catheter 20 described above in the system of FIG. 1.

Figure 3:
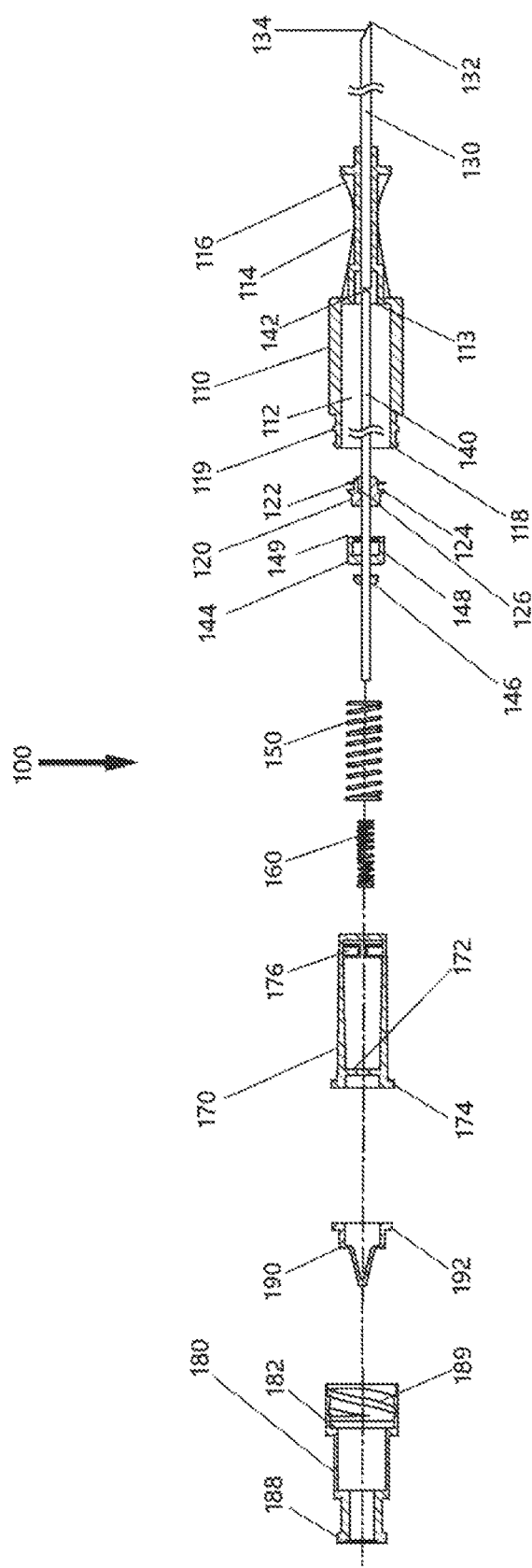
FIG. 3 is a side section exploded view of one embodiment of the present invention.
Figure 4:
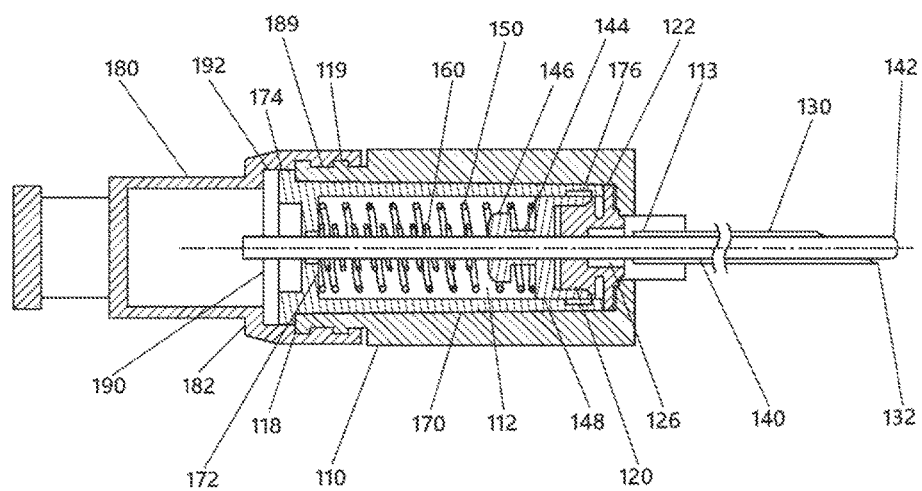
FIG. 4 is a side section view of a second embodiment of the present invention in a fully extended state.
Figure 5:
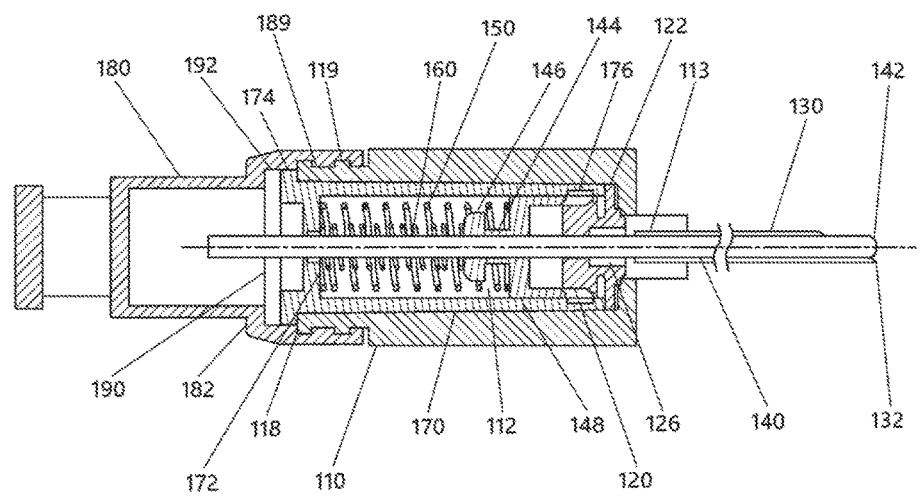
FIG. 5 is a side section view of the second embodiment of the present invention in an indicating state.

Embodiments of a retractable centesis needle device 100 according to the present invention are illustrated in FIGS. 3 to 6. To aid in reference, the end of the device 100 closest to a patient during use shall be considered distal, while the end closest to a user shall be considered proximal. The retractable centesis needle 100 is used to place a catheter (not shown) into a body cavity 90 for extraction of fluid. In some embodiments, however, the device 100 may be used directly to drain body fluid without the use of a catheter. In general terms, the retractable centesis needle 100 is operable through three states. In a fully extended state (FIG. 4), the device is protected from inadvertently puncturing a tissue wall 92. A large spring 150 supplies a biasing force, urging the device toward the fully extended state (FIG. 4). As a user continues to apply force against the tissue wall 92, the large spring 150 begins to compress, and the device transitions to an indicating state (FIG. 5). In the indicating state (FIG. 5), the device provides visual feedback to the user to indicate that further force applied to the device may cause it to transition to a fully retracted state (not shown) and begin to cut through the tissue wall 92. As the device transitions from the indicating state (FIG. 5) to the fully retracted state (not shown), a small spring 160 begins to compress, increasing the biasing force and further urging the device toward the fully extended state (FIG. 4). The indicating state occurs at a point between the fully refracted state and fully indicating state.

Figure 6:
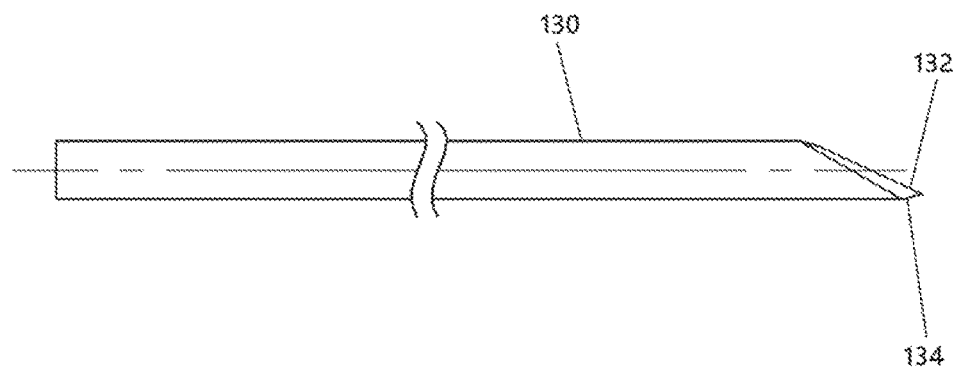
FIG. 6 is a side view of the distal tip of the outer cannula of a third embodiment of the invention.

With reference to FIG. 3, the device 100 comprises a hollow housing 110 having an opening 113 at the distal end. The opening 113 may be through a generally cylindrical projection extending from the distal end of the housing body 110. In one embodiment, the projection may include a luer-type connection to allow the centesis needle to be connected to other devices in a centesis system, such a valve or stopcock. A hollow outer cannula 130 extends distally from the housing 110, and terminates in a sharp tip 132. The angular edge of the sharp tip 132 is adapted to penetrate and cut through body tissues. In some embodiments, an outer edge 134 of the sharp tip 132 is beveled or rounded. FIG. 6 illustrates an alternative embodiment where the tip includes a beveled edge. Beveling provides a softer outer edge that is less likely to damage a catheter during loading, while the inner edge remains sharp to aid in cutting tissues.

The proximal end of the outer cannula 130 protrudes slightly through the opening in the housing 110. In some embodiments, the housing 110 may include a distal grip portion 114, wherein the outer cannula 130 extends through the grip portion 114 to protrude into the main body of the housing 110. The grip portion 114 comprises an elongated body and a pair of concave sidewalls 116 extending from the grip portion 114 to the main body of the housing 110. A sleeve-like needle guard may be placed over a distal portion of the housing 110 to cover the sharp tip 132 while the device is not in use.

The housing 110 has a generally cylindrical cavity 112. An indicator 120 is inserted into the distal end of the cavity 112. The indicator is generally cylindrical in shape, and has a smaller diameter than the cavity 112. In the embodiment depicted in FIG. 3, the indicator 120 includes a flange 122 that is approximately the same diameter as the cavity 112. The flange 122 may further include a beveled edge 124 near the sidewall of the cavity 112. In another embodiment, the indicator 120 may be formed as part of the housing 110. A hole 126 is formed through the indicator 120 to allow passage of an inner cannula 140.

The inner cannula 140 is inserted slidably through the hole 126 of the indicator 120 and the hollow outer cannula 130. The proximal end of the inner cannula 140 extends through the proximal end of the housing 110. The distal end of the inner cannula 140 terminates in a rounded blunt tip 142 extending beyond the sharp tip 132. In the embodiment depicted in FIG. 3, a hub 144 is fixedly attached to the shaft of the inner cannula 140, such as by an adhesive. In an alternative embodiment of the invention, the hub 144 is made of medical grade plastic and is molded onto the inner cannula 140. The hub 144 includes a head portion 146 and a tail portion 148 extending radially from the shaft. The hub tail 148 includes a cavity adapted to fit over the indicator 120. The hub 144 may include a beveled edge 149 configured to mate with the beveled edge 124 of the indicator 120. In at least one embodiment, the hub head 146 and hub tail 148 are connected to form a single hub component, as illustrated in FIGS. 4 and 5.

A large compression spring 150 is positioned within the housing 110 to provide a biasing force. In the embodiment described above, the distal end of the large spring 150 contacts the hub tail 148, and the proximal end of the spring 150 contacts an inner face 172 of a sleeve insert 170. The inner face 172 and/or hub tail 148 may include a seat for the ends of large spring 150, such as a conical protrusion. Since the hub 144 is fixed to the inner cannula 140, the large spring 150 acts to bias the inner cannula 140 distally. The inner cannula 140 is forced to extend until the hub tail 148 comes to rest against the indicator 120, and the inner cannula 140 is in a fully extended state (FIG. 4). The large spring 150 is adapted to be slightly compressed when the device 100 is in the fully extended state (FIG. 4). In some embodiments, one or both ends of the large spring 150 may be connected to the inner face 172 and/or the hub 144. In another embodiment, the ends of the spring 150 are held in place by frictional forces, and the spring 150 may be free to rest on the bottom of the cavity 112.

A second, smaller spring 160 is located within the housing 110 between the inner face 172 and the hub 144. Other elastic biasing components may be used in place of compression springs, such as compressible bulk material or mechanisms providing a spring-like force. In the embodiment depicted in FIG. 3, the hub head 146 is located proximally to the hub tail 148 and separated by a predetermined distance. The small spring 160 is shorter than the large spring 150 by more than the predetermined distance, such that the small spring 160 does not contact the hub head 146 when the inner cannula 140 is in the fully extended state (FIG. 4). Alternatively, the distal end of the small spring 160 may contact the hub head 146, while the proximal end is free and not in contact with the inner face 172 of the sleeve. In either configuration, the small spring 160 may be connected to the sleeve 170 or hub 144 and arranged approximately concentric with the large spring 150. In an additional embodiment, both ends may be unconnected, and the small spring 160 is slidable and free to rest on the inner cannula 140. The inner face 172 and/or hub head 146 may include a seat for the ends of the small spring 160, such as a conical protrusion.

With continuing reference to the embodiment illustrated in FIG. 3, a sleeve 170 is inserted into the cavity 112 of the housing 110. The sleeve 170 is generally cylindrical and hollow and includes openings at both ends. The outer diameter of the sleeve 170 is approximately the diameter of the cavity 112. In one embodiment of the invention, the sleeve 170 is aligned with the housing 110 using a key and notch/keyseat (not shown). A shoulder 174 on the proximal end of the sleeve 170 overlaps a proximal rim 118 of the housing 110. The distal end of the sleeve 170 extends against the flange 122 of the indicator 120 to maintain the indicator 120 in position against the distal end of the cavity 112 as the inner cannula 140 slides through the hole 126. The pressure of the sleeve 170 against the flange 122 provides a seal to prevent fluid leakage into the housing cavity 112. This is advantageous because fluid leakage into the cavity 112 could interfere with the operation of the device. For example, leaked fluid could contribute to a suction effect between the hub 144 and indicator 120 as the inner cannula 140 is retracted, which may cause the indicator 120 to dislodge from its distal resting location at the distal end of the cavity 112 and result in inaccurate indication. Furthermore, the suction effect may increase the amount of force required to retract the inner cannula 140.

A cap 180 is attachable to the housing 110, and secures the sleeve 170 in place. The shoulder portion 174 of the sleeve 170 is placed between the rim 118 of the housing 110 and a shelf portion 182 on the inside of the cap 180. The housing 110 may include external threads 119 corresponding to internal threads 189 on the cap 180. However, other well-known forms of connection may be used such as a detent or pin. The connection between the cap 180 and housing 110 may be further secured by gluing the threaded portions 119, 189 together. The cap 180 includes a valve 190 to prevent the backflow of fluid while the device 100 is inside the body cavity 90. The valve 190 may include a flanged portion 192 to provide a seal between the cap 180 and housing 110. The flanged portion 192 of the valve 190 is secured between the shelf 182 of the cap 180 and the shoulder 174 of the sleeve 170. The valve 190 may be a duckbill type valve, although other one-way valve types may be used. The cap may also include a luer-type connection 188 for attachment to a syringe (not shown).

The inner cannula 140 is movable between the fully extended state (FIG. 4), the indicating state (FIG. 5), and the fully retracted state (not shown). During normal operation of the invention, the large spring 150 biases the hub 144 in a distal direction relative to the housing 110 against the indicator 120. Since the hub 144 is fixedly attached to the inner cannula 140, the large spring 150 also functions to bias the inner cannula 140 causing it to extend distally relative to the outer cannula 130. The large spring 150 is under slight compression while the inner cannula 140 is in the fully extended state (FIG. 4). When the inner cannula 140 is in the fully extended state (FIG. 4), the small spring 160 is not compressed. In the embodiment depicted in FIGS. 4 and 5, the small spring 160 is shorter than the large spring 150, and the hub head 146 is located proximally to the hub tail 148 such that the large spring 150 may be in contact with the hub 144 while the small spring 160 is not in contact with the hub 144. In an alternative embodiment, the large spring 150 may be shorter than or equal in length to the small spring 160, but positioned such that the large spring 160 still contacts the hub 144 before the small spring 160 during retraction. In one such embodiment, the hub tail 148 is positioned proximally to the hub head 146.

When the blunt tip 142 of the inner cannula 140 is pressed against body tissue 92, the tissue 92 imparts a resisting force on the inner cannula 140. A sufficient resisting force pushes the hub tail 148 against the large spring 150 causing it to compress. As the large spring 150 compresses, the device is transitioning from the fully extended state (FIG. 4) to the indicating state (FIG. 5). The blunt tip 142 of the inner cannula 140 is still extended distally beyond sharp tip 132, but begins to be displaced inwardly. When the hub tail 148 is sufficiently displaced, the indicator 120 becomes uncovered, and the device 100 is in an indicating state (FIG. 5).

As the resisting force further increases, the device begins to transition from the indicating state (FIG. 5) into the fully retracted state (not shown), and the hub head 144 contacts the small spring 160 and causes it to compress as well. The small spring 160 may begin to compress when a force of about 0.15-0.35 lbs is applied to the inner cannula 140. In one embodiment, the small spring 160 begins to compress when the force applied to the inner cannula 140 is approximately 0.2 lbs. It will be understood, however, that the present invention is not limited to the specific forces described above, and that the particular forces used may vary depending on the application, for example use on different body tissues. As both springs are compressed, the blunt tip 142 of the inner cannula 140 becomes retracted inside the outer cannula 130, exposing the sharp tip 132. The pressure applied to the sharp tip 132 causes it to cut or pierce through the tissue 92 to allow the outer cannula 130 to pass into the body cavity 90. The inner cannula 140 may continue to retract until the blunt tip 142 is completely within the outer cannula 130, at which point the device 100 is in the fully retracted state (not shown). Once the outer cannula 130 has penetrated the tissue 90, however, the resisting force is removed, and both springs 150, 160 decompress, biasing the inner cannula 140 back toward the fully extended state (FIG. 4).

In one embodiment of the invention, the sleeve 170 includes an indicator window 176 in the sidewall of the sleeve 170 near the distal end. The indicator window 176 is approximately aligned with the indicator 120. As described above, the hub tail 146 is adapted to cover the indicator 120, such that only the hub 144 is viewable through the indicator window 176. As the inner cannula 140 is retracted, the hub 144 is pushed in a proximal direction, and the cavity of the hub tail 148 begins to uncover the indicator 120. In some embodiments, the hub 144 and indicator 120 may be colored in contrasting colors, such as green and red. The use of contrasting colors allows a user to easily see the relative positions of the hub 144 and indicator 120. The change in color through the window 176 signals the user that the inner cannula 140 is beginning to retract, indicating that the device 100 has contacted a tissue wall 92. When the inner cannula 140 is sufficiently retracted, the indicator 120 is completely uncovered such that only the indicator 120 is viewable through the indicator window 176. In one embodiment of the invention, the indicator 120 is completely revealed when the blunt tip 142 and sharp tip 132 are aligned. Full indication during alignment of tips 142 and 132 is advantageous because a user can be certain that the sharp tip 132 is exposed, signaling the user to stop applying pressure or withdraw the device to prevent unnecessary tissue damage. Once the device 100 has passed though the tissue wall 92, the inner cannula 140 will extend again due to the absence of a resisting force. The hub 144 will again cover the indicator 120, signaling to the user that the resisting tissue 92 has been penetrated.

In one embodiment, the housing 110 is made of a transparent material such that the indicator window 176 is directly visible through the housing 110. In another embodiment (not shown), the housing 110 includes a housing window (not shown) aligned with the indicator window 176 of the sleeve 170. The housing window (not shown) and/or indicator window 176 may include a magnifying lens (not shown) to help the user see the indicator 120.

It is understood that the force required to compress a spring is approximately proportional to the change in length of the spring, according to Hooke's law. In a system having a single spring acting on the inner needle, the resulting relationship between displacement and force is roughly linear. In a system having two springs in contact with the inner needle, the combined force is merely the sum of the two spring forces, and still results in a linear relationship. In the prior art device 60 of FIG. 2, for example, a second, smaller spring 74 is placed in opposition to the first spring 72 acting on the inner needle 64. The force of the second spring 74 is merely subtracted from the force of the first spring 72, modifying the slope of the overall force curve but preserving a generally linear profile. A linear force profile is not ideal because it does not provide both high sensitivity to indicate contact with tissue and a high resisting force after the indicator shows contact.

According to the present invention, however, only the large spring 150 is initially compressed by the resisting force because the small spring 160 does not come into contact with both the sleeve 170 and the hub 144. It is not until after a certain amount of displacement that the second spring 160 begins to compress. The addition of the second spring results in a non-linear force profile for the system: between the fully extended state (FIG. 4) and the indicating state (FIG. 5), only the large spring 150 compresses, and a relatively low resisting force causes displacement; between the indicating state (FIG. 5) and the fully retracted state (not shown), both the large spring 150 and the small spring 160 are compressed, and a much higher force is required to achieve the same amount of displacement. It can be appreciated that a spring arrangement according to the present invention results in a lower threshold for indication of tissue contact and a higher threshold for exposure of the sharp tip 132 than in prior art spring arrangements.

If can be further appreciated that in prior art systems using two springs in constant contact, the overall force exerted by both springs against the internal components of the device is higher than in single spring arrangements because both springs contribute to the force. There may be an extended period of time between manufacture of the device and its eventual use in addition to temperature and pressure fluctuations during transport. During the time before use, excessive forces may cause a weakening of components, particularly where separate components are joined together. In addition, the springs may deform to the compressed state, reducing their effectiveness. The present invention, in contrast, has only one spring under constant compression, and because there is not a second opposing spring force, the large spring 150 is only minimally compressed. It is therefore understood that the overall force on the internal components is reduced compared to prior art two spring arrangements, thereby extending the useful life of the invention.

The invention claimed is:
1. A retractable centesis needle comprising:
a housing having a cavity;
a hollow outer cannula extending distally from the housing, said outer cannula being open at both ends and defining a channel therethrough;
an inner cannula slidably disposed within the channel, wherein said inner cannula is adapted to slide between a fully extended state and a fully retracted state;
a first biasing member disposed in the housing cavity, said first biasing member configured to apply force to the inner cannula and biasing the inner cannula distally;
a second biasing member disposed in the housing cavity, said second biasing member configured to variably apply force to the inner cannula wherein the second biasing member distally biases the inner cannula when in the fully retracted state, and wherein the second biasing member does not bias the inner cannula when in the fully extended state.

2. The retractable centesis needle according to claim 1, wherein the distal end of the inner cannula terminates in a blunt tip and the distal end of the outer cannula terminates in a sharp tip, said sharp tip having an outer edge, wherein the outer edge is rounded or chamfered.

3. The retractable centesis needle according to claim 1, further comprising an indicator disposed within the housing cavity, and a hub associated with the inner cannula, said hub adapted to removably cover at least a portion of the indicator.

4. The retractable centesis needle according to claim 3, wherein the indicator is at least partially covered when the distal end of the inner cannula extends beyond the distal end of the outer cannula, and wherein the indicator is completely uncovered when the distal end of the inner cannula is retracted within the distal end of the outer cannula.

5. The retractable centesis needle according to claim 4, wherein the indicator is completely uncovered when the distal end of the inner cannula is aligned with the distal end of the outer cannula.

6. The retractable centesis needle according to claim 3, wherein the indicator and the hub are colored in contrasting colors.

7. The retractable centesis needle according to claim 3, the indicator further including a conical rim configured to accept a distal edge of the hub, and the hub further comprising a head portion and a tail portion, wherein the head portion is proximal to the tail portion, and wherein the second spring is shorter than the first spring.

8. The retractable centesis needle according to claim 7, wherein the hub has a tail portion adapted to contact the first spring and a head portion adapted to contact the second spring.

9. The retractable centesis needle according to claim 3, further comprising a sleeve disposed within the cavity, said sleeve having a window, wherein at least a portion of the indicator is viewable through the window.

10. The retractable centesis needle according to claim 9, wherein the window includes a magnifying lens.

11. The retractable centesis needle according to claim 9, further comprising a cap attachable to the proximal end of the housing and a one-way valve disposed within said cap, wherein said valve is a duckbill type valve.

12. The retractable centesis needle according to claim 11, wherein the cap includes a luer-type connection at the proximal end.

13. The retractable centesis needle according to claim 1, wherein the first and second biasing members are compression springs.

14. The retractable centesis needle according to claim 1, wherein the housing is transparent.

15. The retractable centesis needle according to claim 4, wherein the housing further includes a window, wherein at least a portion of the indicator is viewable through the window.

16. The retractable centesis needle according to claim 9, the indicator further including a flange wherein the distal end of the sleeve is adapted to secure the flange against the housing.

17. The retractable centesis needle according to claim 1, wherein the distal end of the housing includes a luer-type connection.

18. The retractable centesis needle according to claim 1, wherein an indicating state is defined by alignment of the distal end of the outer cannula with the distal end of the inner cannula, the indicating state occurring when the first biasing member is compressed by a force between 0.15 lbs and 0.35 lbs.

19. A retractable centesis needle comprising:
a housing having a cavity;
an indicator disposed in one end of the cavity;
a hollow outer cannula extending from the housing, said outer cannula being open at both ends and defining a channel therethrough;
an inner cannula slidably disposed within the channel, said inner cannula having a hub adapted to cover the indicator;
a first biasing member disposed in the housing cavity, said first biasing member configured to bias the hub in a first direction toward the indicator;
a second biasing member disposed in the housing cavity, said second biasing member configured to bias the inner cannula in the first direction when the indicator is not covered by the hub.

20. A drainage system for centesis procedures comprising:
a catheter having a distal end and a proximal end;
a stopcock coupled to the proximal end of the catheter;
a check valve coupled to the stopcock; and
a retractable centesis needle comprising: a housing having a cavity; a hollow outer cannula extending distally from the housing, said outer cannula being open at both ends and defining a channel therethrough; an inner cannula slidably disposed within the channel, wherein said inner cannula is adapted to slide between a fully extended state and a fully retracted state; a first biasing member disposed in the housing cavity, said first biasing member configured to apply force to the inner cannula and biasing the inner cannula distally; a second biasing member disposed in the housing cavity, said second biasing member configured to variably apply force to the inner cannula wherein the second biasing member distally biases the inner cannula when in the fully retracted state, and wherein the second biasing member does not bias the inner cannula when in the fully extended state, said retractable centesis needle adapted to be inserted through the check valve, the stopcock, and the catheter.

* * * * *